United States Patent [19]

Jansson et al.

[11] Patent Number: 5,104,649
[45] Date of Patent: Apr. 14, 1992

[54] SURFACE-FUNCTIONALIZED BIOCIDAL POLYMERS

[75] Inventors: Robert E. Jansson, Chesterfield, Mo.; Robert N. O'Brien, Victoria; Somyong Visaisouk, Sidney, both of Canada

[73] Assignee: Monsanto Company, St. Louis, Mo.

[21] Appl. No.: 192,440

[22] Filed: May 11, 1988

[51] Int. Cl.$^5$ ................ A01N 33/12; C08F 114/02
[52] U.S. Cl. .................... 424/78.31; 525/331.3; 525/331.4; 525/382
[58] Field of Search ............ 525/331.3, 331.4, 344, 525/382; 424/83

[56] References Cited

U.S. PATENT DOCUMENTS

| | | |
|---|---|---|
| 3,388,080 | 6/1968 | Korosy et al. |
| 3,770,706 | 11/1973 | Walles et al. |
| 3,817,860 | 6/1974 | Lambert et al. ............ 210/29 |
| 3,923,665 | 7/1975 | Lambert et al. ............ 210/501 |
| 4,076,622 | 8/1978 | Costia ......................... 210/501 |
| 4,143,203 | 3/1979 | Rigopulos et al. |
| 4,187,183 | 9/1980 | Hatch ......................... 210/501 |
| 4,190,529 | 10/1980 | Hatch ......................... 210/29 |
| 4,282,366 | 8/1981 | Eudy |
| 4,298,475 | 11/1981 | Gartner |
| 4,349,646 | 9/1982 | Nudel et al. |
| 4,621,120 | 11/1986 | Hollister .................... 525/331.4 |
| 4,663,365 | 5/1987 | Reinehr et al. |
| 4,666,452 | 5/1987 | Nohr et al. ................. 525/344 |

OTHER PUBLICATIONS

Chemical Abstracts 96:40695u (1981).
Chemical Abstracts 100:91069b (1982).
Chemical Abstracts 101:78605z (1984).
Chemical Abstracts 105:75717j (1986).
"Modification of Polyethylene Surfaces with Carbethoxy Substituted Carbenes and Nitrines" *J. of Applied Polymer Science*, vol. 13, pp. 1537-1544 (1969).
"Aminopropylcellulose, Synthesis and Derivatizaiton" *J. Of Polymer Science* vol. 22, 975-984 (1984).
"Liquid Permeation and Separation by Surface-Modified Polyethylene Membranes" *J. of Membrane Science*, 17 (1984) 125-138.
"Influence of Quaternary Ammonium Salts on Cellulose Benzylation" *J. of Polymer Science*, vol. 17, 55-63 (1979).

*Primary Examiner*—Paul R. Michl
*Assistant Examiner*—T. McDonald, Jr.
*Attorney, Agent, or Firm*—Thomas E. Kelley; Richard H. Shear

[57] ABSTRACT

Polymers and articles made therefrom having biocidal surfaces are disclosed wherein the biocidal agent is permanently bonded to the polymer surface. The polymers can be employed to inhibit microbial growth in the adjacent area of the polymer and as disinfectant for fluids such as water. Utility as a contact disinfectant is disclosed.

6 Claims, 1 Drawing Sheet

SURFACE-FUNCTIONALIZED BIOCIDAL POLYMERS

BACKGROUND OF THE INVENTION

This invention relates to polymers and articles prepared from such polymers having permanently bonded to their surface a biocidal agent, processes for making such polymers and methods of use thereof.

Many attempts have been made to functionalize the surface of polymeric articles and for many reasons. The polymeric articles so functionalized have taken many forms such as beads, fibers, or film. In many instances the object of functionalization of the polymer was to provide the articles with biocidal properties. One of the applications for the functionalized polymers is to disinfect water in substitution of chlorine. One attempt to provide such materials is found in U.S. Pat. No. 4,349,646 to Nudel et al. This patent describes a water disinfectant formed from the reaction between a chloromethylated polystyrene or methacrylate and a tertiary amine. A quaternary salt is provided which is taught to be immobilized on the polymer resin carrier. However, in use it has been found that the material is not hydrolytically stable with the result that the quaternary salt leaves the polymer and becomes dissolved in the water.

Another active area of research is the attempt to provide textile fibers with biocidal properties. A recent attempt is described in U.S. Pat. No. 4,663,365 to Reinehr et al. This patent follows others wherein biocidally-active material is incorporated into the spin melt or spin composition employed to make the fiber thereby dispersing the biocidal agent throughout the bulk of the fiber. While some of the biocidal material will be close enough to the surface of the fiber to effect biocidal activity, a large portion of the biocidal material employed is effectively lost because of its being buried in the bulk of the fiber and thereby being separated from the microbes desirably destroyed.

Water purifying devices are being developed because of the concern for pure water available at remote locations. Such a device is described in U.S. Pat. No. 4,298,475 to Gartner wherein a column is fitted with suitable closures on each end and loaded with bactericidal medium such as iodinated cation exchange resin capable of disinfecting the water contained in the column. The biocidal agent is slowly released into the water.

Because cellulose is extensively used in clothing, numerous publications disclose means for modifying the polymer to affect its properties. Cellulosic fabrics have been treated to provide properties such as ion exchange, anti-stat properties, softening and dyeability. A typical disclosure is U.S. Pat. No. 905,200, filed Sept. 9, 1986 and published April 15, 1987 wherein cellulose fabrics are prepared by treatment with solutions of cross-linking agents, acid catalysts and quaternary. amine salts. The anti-microbial properties of grafted cellulose polymers were investigated by N. V. Kolokolkina et al and reported in Zh. Prikl. Khim, 58 (7), pgs. 1603–1606. However, these workers concluded that the lack of anti-microbial activity of the graft polymer was due to the covalent bonds between the cellulose and the grafted polyelectrolyte which prevented diffussion of the polyelectrolyte from the fibrous material to the microbial environment. Labile bonds were suggested.

Contrary to the Kolokolkina et al publication others have provided cellulose derivatives such as hydroxy- ethyl cellulose with bactericidal properties by grafting copolymer material such as 4-vinylpyridine to provide copolymers wherein the vinylpyridine is quaternized with ethyl bromide. Such a process is disclosed in European Patent Application 42075 published June 18, 1980. Anti-bacterial effectiveness of the compounds was demonstrated in vitro. Cellulosic fibers have been modified using linking units which are generally ether linkages although carbon-carbon covalent bonding and nitrogen linking units are also known. Bridging units are generally low molecular weight polyethers such as ethyoxylates but low molecular weights alkalene groups of up to about 3 carbon atoms are also known.

While attempts have been made in the past to functionalize the surface of polymers particularly to provide such surfaces with biocidal activity, a common problem has been the stability of the biocidal agent on the polymer. The attachment of biocidal material to the polymer substrate has been found to be unstable under usual hydrolytic conditions of use causing the material to be released into the liquid media. While it may not present danger since the biocidal materials most commonly employed are relatively safe for limited exposure at low concentration, the surface of the polymer becomes increasingly inactive because of the removal of the biocidal material. There is desired a hydrolytically stable, surface functionalized polymer which may be employed for long periods of time while retaining biocidal activity with a high degree of safety.

SUMMARY OF THE INVENTION

There has now been discovered surface functionalized polymers having chemically bonded to the surface of the polymer biocidally active groups comprising a linking unit adjacent said surface and chemically bonded to the linking unit a biocidal agent. In contrast to the polymers known in the art the surface functionalized polymers of this invention have been found to be hydrolytically stable. Such surface functionalization is provided substantially on the surface only thereby not substantially changing the bulk properties such as the electrical properties of the polymer.

Both synthetic and natural polymers are functionalized in accordance with this invention. Surface functionalized cellulose polymers are provided except that alkalene bridging units are contained within the biocidally active unit, said alkalene group having at least 5 carbon atoms.

The surface functionalized polymers of this invention will generally contain a polymer base which either possesses inherent reactive sites on the surface which become linking units or sites which can, under proper treatment, become reactive with an appropriate linking unit. Under reactive conditions the linking unit reacts with the reactive sites on the polymer surface forming a chemical bond thereto. The linking unit may be an added group having ability to not only react with the reactive sites on the polymer surface but also provide a reactive site on the linking unit onto which biocidal agent or precursor is chemically bonded by further chemical reaction. Also a portion of the reactive site on the polymer may form the linking unit. The linking unit may be separated from the biocidal agent or precursor by any convenient intermediate bridging unit. In some instances it has been found advantageous to provide such bridging unit as will be more fully disclosed below.

The term "biocidally active group" means herein the combination of linking unit, bridging unit if any, and the chemically bound biocidally active agent. In some instances, the biocidal agent or precursor may also supply the bridging unit.

DETAILED DESCRIPTION OF THE INVENTION

Figure 1:
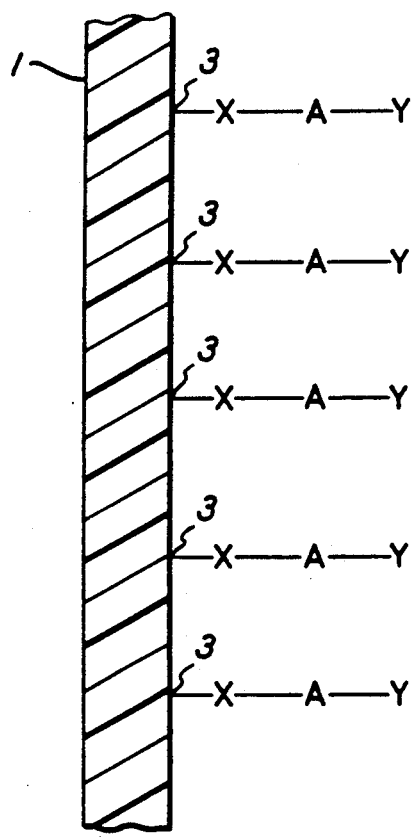
In FIG. 1 there is shown a cross sectional view of a surface functionalized polymer of this invention.

The surface functionalized polymers of this invention are graphically portrayed in FIG. 1 in simplified form wherein 1 is a cross sectional view of a polymer substrate. On the substrate there are reactive sites 3 at the surface of polymer 1. With chemical treatment as will be more fully described below the reactive sites are shown to have been reacted with a linking unit shown in the drawing as X. Chemically bonded to the linking unit X is an optional bridging unit A. Bridging unit A may be an integral part of the biocidal agent or precursor or may be a separate unit added for the purpose of enhancing the properties of the surface functionalized polymer. The biocidal agent is shown in the attached figure as Y chemically bonded to A, if present, or to linking unit X in those embodiments not employing the bridging unit between the biocidal agent Y and linking unit X.

FIG. 1 illustrates the general configuration of the surface functionalized polymers of this invention but is not intended to represent any specific embodiment. Further, while the surface functionalized polymer shown in FIG. 1 is in the form of a film it should be understood that the surface functionalized polymers of this invention may take any form in addition to films such as shaped articles, beads, foams, sintered articles, padding material, blocks, fibers, or any other desired configuration. Further, while FIG. 1 illustrates polymer 1 as being surface functionalized on one surface only it will be evident from the following description that all sides may be functionalized as desired.

Any number of polymers may be employed to prepare the surface functionalized polymers of this invention provided such polymer possesses reactive groups on its surface or that such groups can be activated by appropriate treatment. One of the most commonly encountered polymers and most abundantly available, therefore a preferred embodiment of this invention, is polyethylene. Another commonly employed and abundant polymer useful in making surface functionalized polymers of this invention is cellulose which desirably may possess biocidal activity in accordance with this invention. Other representative polymers include polypropylene, polymethyl methacrylates, polyethyleneglycols, fluoropolymers, rubber, polyvinyl chloride, nylons, polyurethanes, polyesters, polyvinyl alcohols, ethylenevinyl acetate copolymers, ethylene acrylic acid copolymers, silicones and copolymers such as styrenebutadiene, ABS and the like, and those prepared from monomers such as vinylethers, vinylchloroethyl ethers, 2-methyl-1-pentene, vinylpyridines, such as 2-vinylpyridine and 4-vinylpyridine, styrene, acrylates, N-tert.-butylacrylamides, melamine, triacrylates, vinylacetate, 1-pentene, acrylonitrile, other nitrile resins, alpha-methylstyrene, vinyltoluene, vinylidene chloride resins, and the like. Such polymers may be provided in many forms. For example, polyethylene may be provided in sheet, film, particulate, microspheres, sintered or other suitable form.

Typically polymers will have reactive groups on their surface which can be employed to directly react with a linking unit in accordance with this invention. When reactive sites are induced by proper treatment of the surface of the polymer care must be taken to maintain the integrity of the polymer bulk by limiting such treatment to the surface only. Typical examples of such treatment will be described below.

Linking units typically employed in preparing these surface functionalized polymers of this invention include $-SO_2NH-$, $-O-$, $-C-C-$, $-C-N-$, $-C-SO_2-C-$ and the like. Linking units are formed by reacting antimicrobial material or its precursor or a bridging unit with the reactive site on the polymer such as an -OH group to form a hydrolytically stable linkage which in such instance would be an ether linkage. Accordingly, the linking unit may be part of the original polymer which when modified becomes the linking unit or part of the linking unit. In other instances the reactive site is modified to provide an active site for a linking unit to be bonded to the polymer surface. The above-mentioned linking units are employed appropriately depending upon the type of polymer desired to be rendered surface functionalized. For example, polyvinyl alcohol is conveniently surface functionalized by first reacting an —OH group to create a —O— linking unit which forms an ether linkage to the surface of the polymer. Alternatively, polyvinylchloride is conveniently functionalized on the surface with $-SO_2Cl$ followed by an amine to form a sulfonamide with a biocidal agent precursor containing an amine functionality. Other appropriate polymer-linking unit combinations will be obvious to the artisan.

Hydrolytically stable chemical bonds between polymer and linking unit, as well as those bonds joining bridging units A, if any, and antimicrobial agent Y are typically covalent and include the following structural formula:

$-H_2C-SO_2-CH_2-$
$-H_2C-O-CH_2-$
$-H_2C-H_2C-$
$-H_2C-SO_2-NH-CH_2$

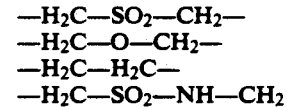

Any number of biocidal agents may be employed to produce a surface functionalized polymer in accordance with this invention. Because of their relative safety, availability and relatively low cost, quaternary amines are commonly employed. Such amines are provided by first chemically reacting the linking unit with an amine precursor and subsequently the amine is quaternized by known means. Other typical biocidal agents employed in this invention are chlorophenol, benzoates, quaternized pyridine, 2-benzyl-p-chlorophenol, 3-methyl-p-chlorophenol, pentachlorophenol, 3,5-dimethyl-p-chlorophenol, p-hydroxybenzoate esters, hexachlorophene, dichloro-phene, trichlorsan, 2-n-octyl-4-isothiazolin-3-one, trichlorocarbanilide, 5-chloro-2-methyl-4-isothiazolin-3-one, 2-methyl-4-isothiazolin-3-one, folpet, 2-mercaptobenzothiazole, sorbate, hexahydro-1,3,5-tris(2-hydroxyethyl)-s-triazine, hexahydro-1,3,5-triethyl-s-triazine, 2-chloro-4,6-bis(ethylamine)-5-triazine, tris(hydroxymethyl)nitromethane, 4-(2-nitrobutyl)morpholine, 1,3-dimethyl-5,5-dimethylhydantoin. Chlorophenol is most conveniently employed in conjunction with a bridging group between the linking unit and the biocidal agent itself. For example, the polyethylene substrate may be functionalized by first reacting the surface of the polymer with a reagent such as sulfuryl chloride or sulfur dioxide and chlorine to provide linking units such as —SOCl. Reacting the linking unit with a polyfunctional bridging unit such as an alkyl diamine and then reacting a substituted chlorophenol with the amine provides the completed biocidally active group.

A large number of quaternary amines are known to possess biocidal activity Any such quaternary amines capable of being bonded to a linking unit or bridging group of the polymers of this invention can be employed. The amine salt extends outwardly from the polymer substrate so as to contact microbial life to be desirably extinguished. In one embodiment of this invention diamine precursors are employed such that one amine group is reacted with the linking unit and the other amine group quaternized in known manner. Suitable diamines are those constituting diamine precursors of the quaternary salts such as those disclosed in U.S. Pat. No. 4,312,813 to Lindemann. As will be more fully described below the amine is preferably quaternized after being reacted with a linking unit thereby permanently bonding the amine to the surface of the polymer.

Referring again to FIG. 1, when the biocidal agent Y is a quaternized amine salt or the polymer is cellulose, it is preferred to employ an alkylene bridging unit A comprising either a separately added unit or a part of the amine precursor such that the salt is separated from the linking unit by at least 5 carbon atoms. In most instances the bridging unit A is an alkylene group having from 2 to about 20 carbon atoms. Although biocidal activity is affected by many factors including a particular biocide-microbe relationship it has been found that improved kill rates are experienced when the bridging unit is alkylene having at least 5 and preferably 6 to 12 carbon atoms. The preferred range of carbon atoms in the bridging unit A results in surface functionalized polymers having increased rate of kill. Biocidally functionalized polymers of this invention may be prepared to control micro-organisms of many varieties including fungi, algae, bacteria, both pathogens and spoilage micro-organisms.

The following is a partial list of typical microbes which can be controlled by contact with the biocidally active group on the surface functionalized polymers of this invention. *E. coli, Pediococcus cerevisiae, Streptococcus fecalis, Streptococcus mutan, Lactobacillus plantarum, Lactobacillus brevis,* Bacillus sp., *Acetobacter aceti, Pseudomonas fluorescens, Pseudomonas fragi,* Pseudomonas sp., *Saccharomyces cerevisiae, Saccharomyces diastaticus, Saccharomyces uvarum,* Aeromonas A440, Aeromonas A440-41, *Klebsiella pneumoniae,* Salmonella LT-2, Salmonella IT-5, *Staphylococcus aureus, Clostridium perfringens.*

The above list of microbes is illustrative only and is not intended to limit the invention in any way. The rate and amount of kill experienced with the surface functionalized polymers of this invention varies with species and medium in which the species is found. Also, as will be more fully explained below molecular structure of the biocidally active group also affects its rate of kill.

The technique for preparing the surface functionalized polymers of this invention varies greatly but all have in common the permanent bonding of the biocidally active group to the surface of the polymer substrate. To illustrate the invention further there is described below by structural representation in Scheme 1 a technique for providing permanently bonded biocidally active groups to a polymer substrate.

In Scheme 1 below reaction 1 results in a linking unit being chemically bonded to a polymer substrate represented by

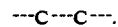

In reaction 2 the linking unit is reacted with an alkyl amine whereby the amine is chemically bonded to the linking unit and in reaction 3 the amine is then quaternized with an alkyl bromide.

Scheme 1

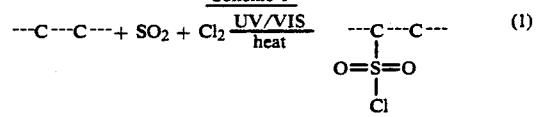

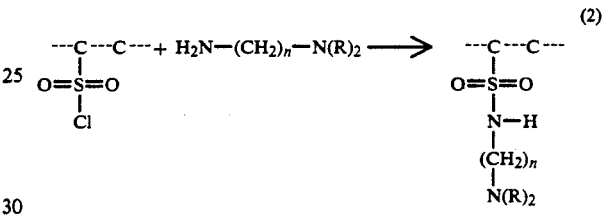

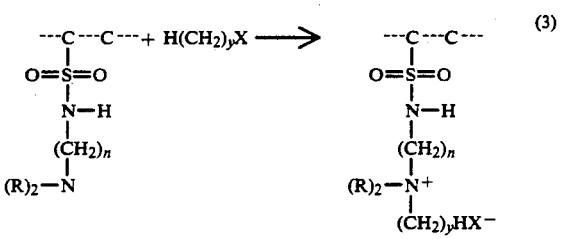

X is a leaving group such as a halogen, R is alkyl or a substituted alkyl group, n and y are integers of at least one and may be the same or different.

As a further example, cellulose, contains a reactive group, the-OH group, on the cellulose backbone. This group is employed to provide cellulose with an ether linking unit to which biocidal groups may be permanently bonded. In this instance the biocidal agent is a quaternized amine which also provides the bridging unit adjacent the linking unit on the polymer. The functionalization of the cellulose begins with a reaction with a base such as sodium hydroxide to form sodium cellulose. This product is illustrated in Scheme 2 below as follows:

Scheme 2

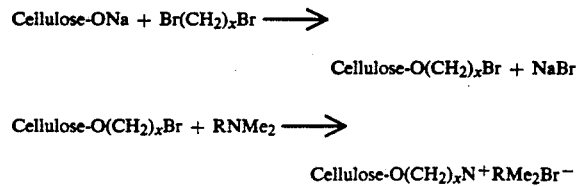

wherein R is an alkyl radical having from 2 to 20 carbon atoms, Me is methyl and x is an integer of at least 5, preferably from 6 to 12 carbon atoms.

Surface functionalized polymers of this invention have been found to be highly advantageous in killing bacteria which come in contact with the biocidal polymer. It is obvious that polymers have many utilities and if permanently biocidal in such utilities they may be highly advantageous. For example, liners for shoes may be prepared from polymers of this invention and thus contribute biocidal activity inside the shoe. Other shaped articles are easily envisioned where biocidal activity is desired.

One of the most advantageous utilities of the surface functionalized polymers of this invention is the sterilization of fluids by simply contacting the fluid with the surface functionalized polymer. By stirring or agitating a fluid so as to provide intimate contact with the surface functionalize polymer of this invention, the fluid is sterilized. In the most advantageous use liquid foods may be sterilized by contacting such food materials to the surface functionalized polymers of this invention. The polymers of this invention may be employed advantageously as packaging material, especially for food packaging. It will be seen that the nature of the permanently bonded biocide is most valuable in sterilization of foods, particularly liquid foods. It has been found that prior attempts to associate biocides with polymer surfaces have resulted in compositions which undesirably release the biocide into the liquid Further, because the polymer releases the biocide from its surface biocidal activity is accordingly depleted However, the surface functionalized polymers of the present invention having chemically bonded, permanently attached biocidally active groups not only provide sterilized food which remain uncontaminated but also preserve the biocidally active group in place for repeated and longer periods of use. In some instances it has been found that proteinaceous liquids may reduce the biocidal activity of the surface functionalized polymers of this invention. In such case the polymer may be regenerated as by flushing the polymer with suitable materials which will wash away any adhering material from the polymer surface. Once regenerated by washing it has been found that the surface functionalized polymer of this invention is again available with little or no loss of biocidal activity for use in further treatment of food products. As employed herein the term "fluid" means gases as well as liquids.

As noted above, the surface functionalized polymers of this invention may take many forms and shapes. In those instances wherein the shape of the polymer is secondary to the biocidal activity the shape of the polymer may be made so as to be conveniently accommodated to the apparatus or conditions of use. That is, for example, sterilization of liquid may be performed by surface functionalized polymers of this invention in the form of small beads. The beads may be placed in cannisters, fluidized bed chambers and the like. Pipe lining, thin film contact units and other embodiments are also envisioned. Other embodiments will become apparent from the following examples.

The invention is further illustrated by the following non-limiting examples wherein surface functionalized polymers are provided and described by reference to FIG. 1.

EXAMPLE 1

Into an agitated vessel containing xylene maintained at 125° C. there were added slowly 90 grams of polyethylene beads (sold commercially by the E. I. DuPont De Nemours Company, Inc. as DuPont 2114 polyethylene). After the mixture became a clear homogeneous solution the solution was cooled to 80° C. and 600 ml of acetone added thereby resulting in the precipitation of polyethylene from solution. The precipitate was in the form of finely divided polyethylene particles and was recovered by filtration, washed with acetone and dried under vacuum.

EXAMPLE 2

Into a 32 ounce Boston round transparent wide mouth soft glass jar was placed 40 grams of polyethylene particles produced in accordance with Example 1. The jar was fitted with a gas feed cap and rotated on a jar roller while the system was purged with nitrogen for 15 minutes.

After nitrogen purge a mixture of sulfur dioxide (100 ml per minute) and chlorine (33 ml per minute) were introduced into the jar for 10 minutes. The system was then illuminated with a quartz UV light for 20 minutes with the chlorine and sulfur dioxide flow rates maintained as noted above. The jar was then purged with nitrogen for 15 minutes and the reaction product slurried in acetone, filtered, washed twice with acetone and then dried under vacuum overnight.

EXAMPLE 3

In a 3 liter flask N,N-dimethylaminopropylamine (134 ml) was diluted to a volume of 600 ml with petroleum ether and added to 200 grams of polymer sulfochlorinated according to the procedure of Example 2. After diluting to a volume of 2 liters with additional petroleum ether the mixture was stirred at room temperature for 2 hours under a nitrogen blanket The product was then filtered, washed successively with petroleum ether, methanol, then again with petroleum ether and dried under vacuum.

EXAMPLE 4

The aminated product from Example 3 was placed into a 2 liter flask fitted with stirring apparatus, means to provide a nitrogen blanket and an oil bath to control temperature. To the flask were added 1-bromododecane (500 grams) and acetonitrile (1 liter) and the reaction mixture stirred for 24 hours at 42° C. The resultant product was filtered, washed successively with petroleum ether and acetone, then dried under vacuum to provide surface functionalized polyethylene possessing biocidal activity in accordance with this invention. The linking units X are —$SO_2NH$— groups and the biocidal agent Y is —$^+N(CH_3)_2C_{12}H_{25}Br^-$ units A.

EXAMPLE 5

Microspherical polyethylene (20 grams) sold commercially under the trade name FN-524 by U.S.I. Chemical Company was sulfochlorinated and recovered as described in Example 2 with the exception that the imbibition time for sulfur dioxide and chlorine was 40 minutes. A second batch of microspherical polyethylene was likewise treated and recovered.

To the combined product obtained above was added 35.4 grams of N,N-dimethylaminopropylamine in 200 ml of petroleum ether. After stirring for 2 hours at room temperature under nitrogen, the product was filtered, washed successively with petroleum ether, methanol and again with petroleum ether A portion (20g) of the aminated product was slurried in bromohexadecane (40g) at 42° C. for 24 hours. The resultant quaternized product was filtered and washed successively with petroleum ether and then acetone and finally dried under vacuum. Linking units X and bridging units A are as indicated for Example 4 which the biocidal agent is $-^+N(CH_3)_2C_{16}H_{33}Br^-$.

EXAMPLE 6

(Prior Art)

Into a 500 ml round bottom flask was placed 56 grams of 42% 3-(trimethoxysilyl) propyldimethyl-octadecyl ammonium chloride (sold commercially under the trade name DC 5700 by Dow Corning Company), 35 grams of cellulose and 224 grams of acetonitrile. This mixture was refluxed overnight and the product filtered, washed with acetonitrile and Soxlet extracted overnight with acetone. The procedure produced surface functionalized cellulose.

EXAMPLE 7

The sulfochlorination of FN-514 polyethylene was repeated according to the procedure of Example 5 with the exception that the UV irradiation extended to 80 minutes. The resultant sulfochlorinated product was refluxed (first reflux) in acetonitrile (120 ml) which contained 20 g diaminobutane for 3.5 hours under a nitrogen blanket. The product of the first reflux reaction was filtered, washed 4 times with acetonitrile and dried under vacuum. Ten grams of the aminated product obtained from the first reflux reaction was then placed into 150 ml of acetonitrile containing 10 grams of 3-chloro-4-hydroxyphenylacetic acid and refluxed (second reflux) overnight The product of the second reflux reaction was then filtered, soxlet extracted with ethanol for 4 hours and then dried under vacuum. There is provided a surface functionalized polyethylene wherein the linking units X are —SO$_2$NH—, the bridging units A are

and the biocidal agent is o-chlorophenol groups.

EXAMPLE 8

Microspherical polyethylene was sulfochlorinated and reacted with 1,4-diaminobutane as described in Example 7. Into a reflux vessel were added 10 grams of the reacted microspherical polyethylene and 3 grams of terephthaloyl chloride. The mixture was then refluxed in 150 ml of acetonitrile under nitrogen overnight. The product of the reflux reaction was filtered and washed with three 100 ml portions of hot water at 90° C. to hydrolyze the acid chloride and remove by-product hydrochloric acid. The product was washed with three 100 ml portions of warm (70° C.) acetonitrile and dried under vacuum. The product obtained is a surface functionalized polyethylene with benzoic acid biocidal groups Y attached to —SO$_2$NH-linking units X through

bridging units A.

EXAMPLE 9

The procedures of Examples 2, 3 and 4 were repeated with the exception that 40 grams of small particle polyvinyl chloride were employed in place of polyethylene. There was observed some discoloration of the polymer in the amination step. There was provided surface functionalized polyvinyl chloride having permanently bonded to its surface a biocidal quaternary ammonium salt wherein linking and bridging units X and A as well as biocidal agent Y are the same as described in Example 4 above.

EXAMPLE 10

The procedure of Examples 1 and 2 is repeated with the exception that the polyethylene was in the form of a 3 mil thick film cut into strips one inch wide and 6 inches long. The sulfochlorinated strips were submerged in a mixture of 1600 ml of petroleum ether and 300 ml of 3-dimethylaminopropyl amine for 2 hours at room temperature. The film was then washed successively with petroleum ether, methanol and again with petroleum ether and dried. The dried film was then immersed in 1-bromohexadecane warmed at 50° C. for 24 hours. The film strips were then removed, washed successively with acetone, petroleum ether and again with acetone then dried. There was produced surface functionalized polyethylene films having linking and bridging units X and A as well as biocidal agent Y as described above in Example 5.

EXAMPLE 11

This example demonstrates the lack of the electrical property of bulk ionic conductivity of the surface functionalized polymers of this invention. There is provided below comparative resistance measurements in an electrolytic cell employing platinum electrodes and a 3 mil thick membrane dividing the cell into 2 portions. Into each portion of the cell was placed 0.1 M sodium chloride aqueous solution as an electrolyte.

Three films were employed to divide the cell which were polyethylene, the product of Example 10 and a commercial ion exchange membrane sold under the trade name Nafion by E. I. DuPont De Nemours and Company, Inc. Resistance measurements between the cell portions were provided by means of a Beckman industrial megohmeter. The results of the measurements are presented in the table below.

TABLE 1

| FILM | RESISTANCE |
|---|---|
| polyethylene | $10^7$ megohm |
| polyethylene of Ex. 10 | $10^5$ megohm |
| Nafion | <.5 megohm |

The data presented in the table above shows that the polyethylene bulk ionic conductivity as compared to such property of surface functionalized polyethylene of Example 10 is not significantly different.

EXAMPLE 12

Figure 2:
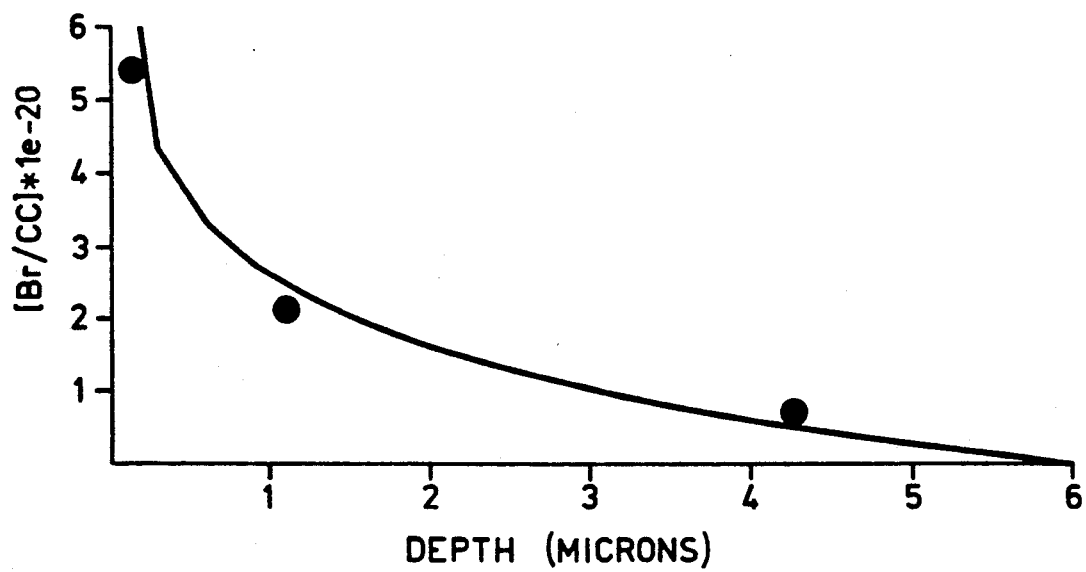
In FIG. 2 there is shown graphically data obtained by Rutherford Backscattering Studies of the polymer films of this invention.

To further demonstrate the exclusive surface functionalization of polymers of this invention a Rutherford Back Scattering Study was performed on the polymer of Example 10. In this procedure an energetic beam of helium nuclei is directed at the film and the intensity of the back scattered beam is measured. The intensity of back scattering is a function both of the atomic mass of the atom hit by the helium nuclei as well as the distance of the atom from the surface of the sample. A plot of bromine concentration as a function of depth provides data whereby it is possible to fit a logrithmic decay function to the data. The data obtained from the study is presented in FIG. 2. From the data in FIG. 2 it is reasonable to assume that within about 6 microns from the surface bromine concentration becomes extinct. According to this data surface functionalization is observed because of the presence of bromine in an extremely small fraction of the total film thickness thereby confirming the lack of bulk functionalization as indicated by the results in Example 11.

EXAMPLE 13

Prior Art

To provide a contrast with the surface functionalized polymers of the present invention there is prepared a Merefield resin in accordance with a procedure taken from U.S. Pat. No. 4,349,646 to Nudal et al. In this procedure 5 grams of Merefield resin was stirred at room temperature in dioxane for 48 hours. The mixture was cooled to 0° C. and then 75 ml of dimethyloctylamine which had been precooled to 0° was added. This mixture was stirred for additional 48 hours at 0° C. After allowing the mixture to attain room temperature it was filtered and then resuspended in 2M hydrochloric acid and stirred for an additional 48 hours. The product was then filtered, washed with three 50 ml portions of 2M hydrochloric acid, three 50 ml portions of 0.1 N sodium hydroxide, five 50 ml portions of 2M sodium chloride and then with deionized water until the filtrate was nearly chloride ion free. The material was then dried at 60° C. under vacuum.

EXAMPLE 14

This example demonstrates the hydrolytic instability of prior art polymers treated to provide biocidal functionality as well as the hydrolytic stability of the surface functionalized polymers of this invention.

The following test is based on the fact that quaternary ammonium salts form a colored complex with tetrabromophenolsulfonphthalein which is commonly known as a color indicator by the shortened name bromphenol blue. The complex formed by quaternary salts and bromphenol blue can be extracted into organic solvents while the sodium salt of bromphenol blue does not. The method detects quaternary ammonium salts in amounts as low as in the range of from 0.08 to 8 micromoles and is published by Dow Corning Corp., Midland, Mich., as Corporate Test Method 0824 (AMINE-quaternary Colorimetric).

In accordance with the procedures, one gram samples of treated polymers were tested. Each were slurried in 10 ml of aqueous buffer at pH 3 at 50° C., held overnight, and then filtered. The filtrate obtained from each sample was tested for soluble quaternary ammonium ion according to the below-described procedure. The results of the test appear in Table 2 below.

In the test procedure one ml of the filtrate to be tested is diluted to 10 ml with water. A solution of bromphenol blue is prepared by combining 4 grams of bromphenol blue and 1 liter of water. Then, 2 ml of an aqueous sodium carbonate solution at a concentration of 10% and 1 ml of the bromphenol blue solution are added to the sample and mixed thoroughly The solution is extracted with 10 ml of methylene chloride.

Color in the organic layer is a positive test for quaternary amine in the test sample. A portion of the organic layer from the blank is removed to fill a 1 cm cell. A duplicate 1 cm cell is filled with a portion of the organic layer from the sample. The light absorbance of the blank and duplicate samples is measured at 604 mu or the 700 to 400 mu is scanned using the base line technique.

TABLE 2

| Example No. | Color Detected |
|---|---|
| 6 | yes |
| 13 | yes |
| 4 | no |

The results shown in Table 2 indicate the hydrolytic instability of prior art functionalized polymer materials.

EXAMPLE 15

Sulfochlorinated polyethylene was prepared in accordance with Example 2. Amination reactions were carried out in each case by mixing a ten gram sample of the sulfochlorinated polyethylene with 0.1 moles of the appropriate ω-dimethylaminoalkyl amine in 60 ml of petroleum ether at room temperature for too hours. The aminated product was filtered, washed twice with petroleum ether, twice with methanol and again with petroleum ether. After drying overnight under a nitrogen sweep, the aminated product was quaternized by mixing with the appropriate alkyl bromide (70 g) at 40° C. for twenty-four hours. The quaternized product was filtered, washed twice with petroleum ether, twice with acetone, again with petroleum ether and then dried overnight under a nitrogen purge.

The above procedure provided a series of biocidally active polymers represented by the following structural formula:

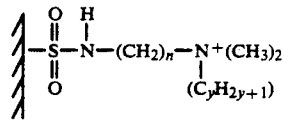

EXAMPLE 16

The polymers produced in accordance with the procedure of Example 15 were tested to determine biocidal activity against various bacteria. The bacteria cultures were prepared as follows:

A. Preparation of Cells

Subcultures of all cell strains were taken from stock cultures and put into trypticose soy agar (TSA), TSA plus 0.25% glucose or MRS agar (de Jar. Rogosa, Sharpe Chemical Co.), depending on each strain's requirements approximately every 3 months or whenever signs of abnormality appeared. These subcultures were kept at 4° C. and were subcultured every 2 weeks to provide cells of about 1-2 weeks of age for experimental use. The cultures used for experiments were inoculated by taking one or two colonies from the subculture plate using an inoculating loop, and transferring the colony to a 5 ml tube of trypticose soy broth (TSB), lactobacillus broth or MRS broth, as appropriate. Depending on growth rate the cell suspension was aged for 7 to 8 hours or 17 to 24 hours to obtain a viable culture of cells in stationary phase. Incubation was conducted at temperatures of 30° C. or 37° C. with shaking or no shaking depending upon optimal requirements of each organism A 1/100 inoculum of these cells was then transferred to a 30 ml flask of the same medium and these cells grown up in similar conditions except the time for aging was 17-48 hours to produce a quantity of cells in stationary phase for experimental use.

Prior to use, the cells were harvested by centrifuge (at least 10,000 rev/minute for 5 minutes), decanting the supernatant liquor and washing the cells twice in cold 0.01 M phosphate buffered saline (PBS), at pH 7.4. The cells were then resuspended to the approximate original volume in PBS. The $O.D._{450}$ of the cell suspension was measured and from this the concentration of the cell suspension was determined. The final cell suspension was kept on ice until it was required.

B. Apparatus

Sterile 125 ml flasks were employed. They were immersed in a constant temperature water bath equipped with a mechanical agitation for the flasks which maintained gentle motion of the contents of the flask. The water bath was held at 30° C.

C. Procedure

Into each flask was placed about 0.1 gram of a surface functionalized polymer (powder) prepared as described in Example 15 above which had been sifted through a 630 um mesh sieve. A control flask which did not contain any powder was also run. Approximately 45 to 49.5 ml of .01 M PBS was added to each flask and they were then put into the water bath and allowed to shake gently for 30 to 45 minutes. Then cells were added to provide the desired concentration and to give 50 ml of fluid per flask. The cell concentration was provided by adding about 5 ml of liquid containing $2.5 \times 10^4$ cells/ml.

Samples were removed from the flask at time intervals indicated in the table below. The samples removed from the flasks were spread onto predried agar plates containing an appropriate medium and incubated at 30° C. or 37° C. for 24-48 hours or until colonies were large enough to be counted. Initial cell count was established by a colony count from the control flask taken after one minute in the water bath. Such count represents 100% cell survival for each experiment.

D. Results

In the table below there is listed for the various strains of bacteria employed in the above-described experiment survival rate expressed as percent of initial cell culture. This was determined by dividing the count for the particular test flask by the count for the control flask at one minute multiplied by 100. The results reported in Table 3 below were obtained by employing compounds of Example 15. In Table 3 below the variables n and y are indicated for each biocidal unit. In all tests with polymers of Example 15 regardless of the values of n and y bacteria population were significantly reduced during the timed experiments. The percentages of bacteria population varied with the values of n, y and the type of bacteria.

TABLE 3

| POLYMER | | % Survival (2 hr/4 hr) of Bacteria ($2.5 \times 10^3$ per ml) in 50 ml PBS | | | | | | | |
|---|---|---|---|---|---|---|---|---|---|
| | | | | *Pseudomonas* | | | *Proteus*[1] | *Lactobacillus* | *Micrococcus* |
| n | y | Aeromonas | Klebsiella | *Fluorescens* | Salmonella | *E. Coli*[1] | *Mirabilis* | *Plantarum* | *Luteus* |
| 3 | 8 | (1/0.1) | (54/31) | (32/17) | (67/54) | (7) | | (65/11) | (15/1) |
| 6 | 8 | (1/0.4) | (46/23) | (37/11) | (70/62) | (3) | | | |
| 6 | 12 | (2/0.6) | (48/25) | (56/36) | (55/54) | (7) | | | |
| 7 | 12 | (2/0.7) | (54/33) | (45/31) | (75/56) | (7) | | | |
| 11 | 8 | (1/0.5) | (79/65) | (10/2) | (69/67) | (24) | | | |
| 3 | 12 | | | | | (21) | | | |
| 5 | 12 | | | | | (5) | | | |
| 11 | 12 | | | | | (43) | | | |
| 3 | 6 | | | | | (37) | | | |
| 3 | 10 | | | | | (6) | | | |
| 3 | 12 | | | | | (36) | | | |
| 3 | 16 | | | | | (33) | (20) | (40/5) | |
| 4 | 8 | | | | | (36) | | | |
| 5 | 8 | | | | | (23) | | | |
| 7 | 8 | | | | | (3) | | | |
| 12 | 8 | | | | | (80) | | | |

[1] 4 hour survival data only

EXAMPLE 17

In the same manner as described above in Example 17, biocidal polymers prepared in other examples were tested to determine their biocidal activity against *E. coli* bacteria. In Table 4 below are presented results of tests conducted by the procedure of Example 17 showing the biocidal activity of various biocidal polymers of this invention.

TABLE 4

| % SURVIVAL (4 Hr.) OF *E. COLI* ($2.5 \times 10^3$ PER ML) IN 50 ML PBS | |
|---|---|
| Example # | % SURVIVAL |
| 7 | 33 |
| 8 | 32 |

EXAMPLE 18

The surface of polyvinylbenzylchloride (PVBC) is chemically modified to provide reactive sites onto which linking groups may be placed for the purpose of providing the surface of the polymer with biocidally active agents. The polymer is normally unreactive and in order to provide surface modification the polymer is first treated to provide such reactive sites. Generically the reaction may be described as follows.

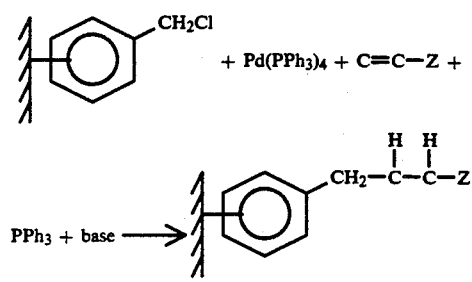

wherein $PPh_3$ is triphenyl phosphine, and Z is a reactive group such as $C \equiv N$ or a carboxylate.

In a Fisher-Porter bottle were mixed 500 mg of PVBC, 1,415 mg of methyl acrylate, 34 mg of PPh$_3$ and 1,056 mg of proton sponge. The mixture was degassed and 76 mg of Pd(PPh$_3$)$_4$ was added under a slow flow of argon. The bottle was capped with a pressure gauge and heated to 125° C. for 17 hours and then cooled to room temperature. The solvent was removed on a rotary evaporator and the residue was washed thoroughly with diethyl ether, filtered and dried on a vacuum line. Infrared analysis shows a strong carbonyl absorption at 1734 cm$^{-2}$. The above reaction can also be performed using acrylonitrile wherein infrared analysis shows a strong absorption at 2220 cm$^{-1}$ indicative of the incorporation of a nitrile. The carboxylate is then reacted with an appropriate biocidal agent precurser. Such precursers may be alkyl diamines which are subsequently quaternized. A nitrile may be hydrogenated to form an amine which is subsequently quaternized.

Because of the large number of polymers and biocidally active groups thereon in accordance with this invention numerous practical uses are envisioned. As mentioned above, polymers of this invention are greatly advantageous in the food processing and packaging industry because the biocidally active groups of the surface modified polymer do not contaminate the food material being processed or packaged Further, container lining may be employed where non-polymeric containers are required. On the other hand where the container is comprised of polymeric material the container itself may be surface modified at some stage of manufacture so as to provide biocidally active articles. Thus, septic hardware may be fashioned.

The surface modified biocidally active polymers of this invention may be employed to resist bacterial growth in such common articles as garbage containers, sponges, diapers, feminine hygiene apparel, bandages, contact lens containers and surgical dressing. Manufactured articles such as carpet, clothing, especially hospital gowns, etc. are particularly advantageous when made of biocidally active polymers of this invention. Polymeric woven and non-woven fabrics may be prepared wherein the polymer possesses biocidal activity in accordance with this invention.

Other practical applications to which the biocidal polymers may be directed are in the manufacture of floor tile, in the operation of cooling towers and in many other such uses where long term biocidal activity is desired.

What is claimed is:

1. An article having a polyethylene surface and biologically active quaternary amine groups which are grafted to said surface by sulfonamide groups.

2. An article according to claim 1 wherein said sulfonamide group is of the structure —SO$_2$NH—.

3. An article according to claim 1 wherein said amine groups are grafted by sulfonamide linking group and an alkylene bridging group.

4. An article according to claim 3 wherein said linking group and said bridging group are combined in the structure
—SO$_2$—NH—(CH$_2$)$_n$—, wherein n is 1 to 20.

5. An article according to claim 4 wherein said amine group comprises one alkyl group of 6, 8, 10, 12 or 16 carbon atoms.

6. An article according to claim 5 wherein said amine group further comprises two methyl groups.

* * * * *